United States Patent [19]

Holtkamp, Sr.

[11] Patent Number: Plant 7,685

[45] Date of Patent: Oct. 22, 1991

[54] AFRICAN VIOLET PLANT NAMED IMPROVED MONTANA

[76] Inventor: Reinhold Holtkamp, Sr., Blumenstrasse 28, D 4242 Rees-Haffen, Fed. Rep. of Germany

[21] Appl. No.: 565,313

[22] Filed: Aug. 10, 1990

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner

[57] ABSTRACT

A new and distinct cultivar of African violet named Improved Montana characterized by its single, violet-shaped, shiny white flowers; strong, upright flower stems that curve slightly toward the center to form a compact bouquet above the leaves; bright green, oval to spear-shaped leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Improved Montana.

The new cultivar was referred to during the breeding and selection process by the designation M/E 18/1 and is a product of a planned breeding program. The basic objective of the breeding program was to create a new African violet cultivar improving certain characteristics of the cultivar Montana, disclosed in my U.S. Plant Pat. No. 4,351, granted December, 1978. The new cultivar was originated from a cross made by me in the controlled breeding program in Haffen, Federal Republic of Germany. The female, or seed parent was a cultivar designated b 296 SAM blue. The male, or pollen parent was a cultivar designated FEDA blue upright.

Improved Montana was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Improved Montana has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of Improved Montana, which in combination distinguish this African violet as a new and distinct cultivar:

(1) Strong, upright flower stems curving slightly toward the center.

(2) Single, violet-shaped, shiny white flowers.

(3) Each plant carries 9–11 and more upright flower stems each of which carries 10–12 and more flowers.

(4) Long lasting, non-dropping flowers.

(5) Vigorous and compact grower.

(6) Plant saleable 10 to 11 weeks after potting.

(7) Seed capsules push slightly through.

(8) Oval to spear-shaped, bright green leaves.

(9) After maturity the flowers dry off, and remain on the peduncle without becoming infected by botrytis.

The new cultivar is most similar to, and was specifically intended to improve upon the characteristics of, my previously patented cultivar Montana. In comparison to Montana, the new cultivar is principally distinguished by its more compact growth habit, smaller blooms, larger leaves, fuller bouquet and by its longer flowering period.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Improved Montana.

Parentage:

*Male parent.*—FEDA blue upright.

*Female parent.*—b 296 SAM blue.

Propagation: The new cultivar holds its distinguishing characteristics through successive propagations by leaf cuttings.

Plant: From 9 cm to 11 cm tall when grown in pots, and approximately 24–28 cm in diameter when fully grown.

*Leaves.*—General form: Oval to spear-shaped. Diameter: 60–70 mm wide, 70–80 mm long. Texture: Velvety. Aspect: Hairy, shiny, slightly serrated. Veins: Upperside: well visible; underside: very well pronounced, light green, shiny. Color (upperside): Yellow-Green Group 147 A to B. Color (underside): Greyed-Green Group 194 D. Petiole: Strong, light green, hairy.

*Flowers.*—Buds: Bell-shaped, 7–9 mm just before opening, greenish white. Sepals: Five (5). Color: Green. Calyx: Shape: Funnel-shaped. Aspect: Spear-shaped, hairy. Peduncle: Character: Strong upright, hairy. Color: Green.

*Individual flowers.*—Size: 35–40 mm. Shape: Single violet-shaped (3 large, 2 small petals) Color (upperside): Shiny white. Color (underside): Shiny white. Borne: Each flower stem carries 10–12 and more flowers on strong, upright peduncles that are free standing above the leaves, thereby forming a compact bouquet. Flowering habit: Flowers 10–11 weeks after potting.

Reproductive organs:

*Stamens.*—Two (2). Anthers: 2 composed of 4 anther cells, seed capsule pushes slightly through.

*Filaments.*—Yellowish white, 4 mm long.

*Pollen color.*—Yellow Group 7 A.

*Styles.*—6–7 mm long, white, base of ovary light green and hairy.

Roots: Normally developed, white when young, turning slightly brownish when older.

Disease resistance: Up to date, Improved Montana has shown very good resistance to all major violet diseases.

General observations: Improved Montana is a very attractive, vigorous and compact grower with single violet-shaped, shiny white flowers and bright yellow anthers. A tight bouquet of flowers free standing above the leaves develops after approximately 10–11 weeks. Each of the 9–11 and more strong flower stems carries 10–12 and more flowers. The flowers are long-lasting and non-dropping. Bright green, oval to spear-shaped leaves surround the bouquet and give the plant a fresh look.

I claim:

1. A new and distinct cultivar of African violet named Improved Montana, as described and illustrated, and particularly characterized by its single, violet-shaped shiny white flowers; strong, upright flower stems that curve slightly toward the center to form a compact bouquet above the leaves; bright green, oval to spear-shaped leaves; profuse flowering, vigorous and compact growth habit, flowering 10–11 weeks after potting, and its long lasting and non-dropping flowers.

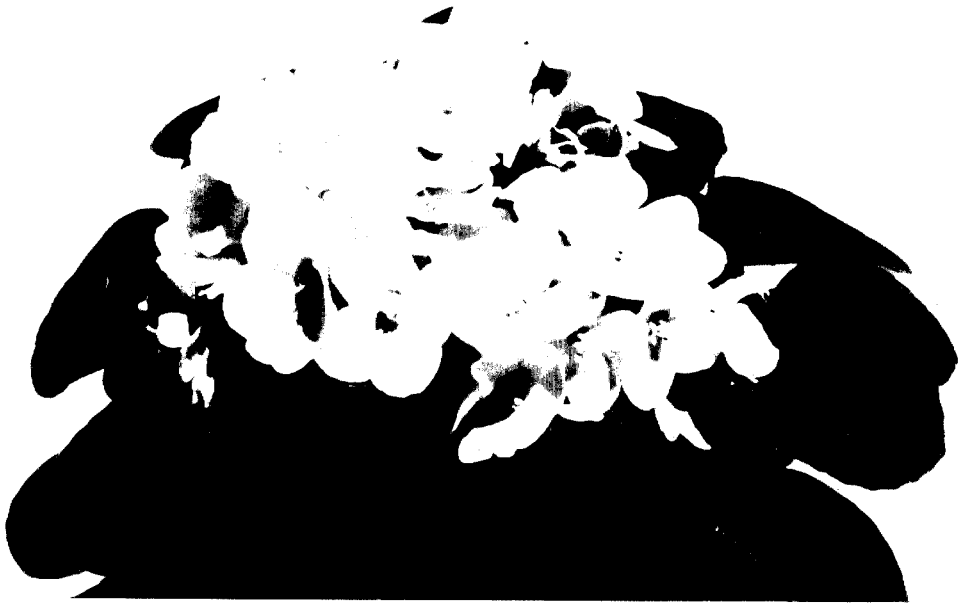

* * * * *